US008430915B2

(12) United States Patent
Beaurain et al.

(10) Patent No.: US 8,430,915 B2
(45) Date of Patent: Apr. 30, 2013

(54) SPINAL OSTEOSYNTHESIS DEVICE AND PREPARATION METHOD

(75) Inventors: Jacques Beaurain, Chapelle (FR); Joel Delecrin, Vertou (FR); Michel Onimus, Besançon (FR); Isabelle Koenig, L'Etrat (FR); Alain Ducolombier, Antony (FR); Marc Pierunek, Montpellier (FR); Hervé Chataigner, Boussieres (FR); Marielle Derosi, Perols (FR); Agnès De Postel, Waly (FR)

(73) Assignee: LDR Medical, Rosiéres Prés Troyes (FR)

( * ) Notice: Subject to any disclaimer, the term of this patent is extended or adjusted under 35 U.S.C. 154(b) by 757 days.

(21) Appl. No.: 12/409,327

(22) Filed: Mar. 23, 2009

(65) Prior Publication Data

US 2009/0182381 A1    Jul. 16, 2009

Related U.S. Application Data (63) Continuation of application No. 10/473,999, filed as application No. PCT/IB02/02827 on Apr. 3, 2002, now Pat. No. 7,507,248.

(30) Foreign Application Priority Data

Apr. 6, 2001 (FR) ...................................... 01 04717

(51) Int. Cl.
*A61B 17/70* (2006.01)

(52) U.S. Cl.
USPC ........................................... 606/267; 606/246

(58) Field of Classification Search .................. 606/246, 606/250–279
See application file for complete search history.

(56) References Cited

U.S. PATENT DOCUMENTS

| 5,282,863 | A | * | 2/1994 | Burton | 606/254 |
| 5,578,033 | A | * | 11/1996 | Errico et al. | 606/276 |
| 5,603,714 | A | * | 2/1997 | Kaneda et al. | 606/272 |
| 5,651,789 | A | * | 7/1997 | Cotrel | 606/252 |
| 5,876,403 | A | * | 3/1999 | Shitoto | 606/308 |
| 6,074,393 | A | * | 6/2000 | Sitoto | 606/307 |
| 6,458,132 | B2 | * | 10/2002 | Choi | 606/267 |
| 6,475,218 | B2 | * | 11/2002 | Gournay et al. | 606/272 |

* cited by examiner

*Primary Examiner* — Kevin T Truong
*Assistant Examiner* — Michael Araj
(74) *Attorney, Agent, or Firm* — Denko Coburn & Lauff LLP (57) ABSTRACT

A spinal internal implantation device for osteosynthesis has one or more bars for supporting for moving the spine and at least one implant for connecting the bars and vertebrae. The implant includes a blown anchor attached to a body of the implant and a fixation arrangement for the bars. The fixation arrangement includes a clamp for clamping the bar against internal walls of a channel formed in the body of the implant. At least part of the length of the bars includes a transversal bearing structure that is a cross-section of the bars having at least one flat part of a part having a lower forepost convexity than the rest of the cross section.

45 Claims, 4 Drawing Sheets

SPINAL OSTEOSYNTHESIS DEVICE AND PREPARATION METHOD

CROSS-REFERENCE TO RELATED APPLICATIONS

This application is a continuation of U.S. patent application Ser. No. 10/473,999, filed Apr. 12, 2004 now U.S. Pat. No. 7,507,248, which claims priority to International Application PCT/IB02/02827, filed Apr. 3, 2002, which claims priority to French Patent Application No. 0104717, filed Apr. 6, 2001.

BACKGROUND

The present invention relates to an osteosynthesis device, particularly for spinal support or correction, that can be used in particular for internal implantation.

For spinal support or correction, a device comprising one or more support bars positioned along the spinal column is used, and fixed to certain vertebrae by implants. Said implants are fixed at one end to the bars and at the other end to the vertebrae by bone anchorage means, composed of a hook supported by a vertebra or of a threaded part screwed inside the vertebra itself, for example at the pedicle.

In such devices, it is known to use bars inserted into the body of the implant via an opening, either simply through the implant or in the form of a channel opening onto a side, said channel possibly opening onto the side or rear (on the top of the implant).

In the case of a closed type implant, the insertion of the bar must most frequently be carried out after the fixation of the implants, which requires the delicate operation of deforming the bar as it is inserted into the different implants.

In the case of an implant with a side or rear opening, the bar-implant fixation may be obtained by means of an intermediate part referred to as a clamp. Said clamp is formed from a ring which is inserted around the bar and fixed to it by a clamping screw, said clamp in turn being inserted into the opening of the implant longitudinally along the axis of the bar. Once the clamp is inserted longitudinally in the implant, as in patent FR 2 545 350, the clamping is obtained by a conical shank and secured by an additional part referred to as a safety lock. Failing a safety lock, as in patent EP 0 392 927, the clamping is secured by two additional screws clamped onto the bar via the clamp and the body of the implant.

Another possibility consists of inserting the bar directly into an implant with a rear open channel, as in patent FR 2 680 461, and clamping this bar with a threaded plug securing the bar by means of a curved blade to provide a satisfactory contact surface.

In both cases, this assembly of several parts is intended to ensure the reliability of the clamping, but represents a complexity and size liable to render implantation delicate, particularly at the junction of the lumbar and sacral regions where only a small amount of space is available due to anatomical conditions. The presence of small parts to assemble during the operation involves the disadvantage of more delicate manipulations and the risk of said small parts being disseminated in the operative field.

SUMMARY

An aim of the present invention is to remedy the drawbacks of the prior art by providing an osteosynthesis device enabling easier adjustment on the operative site and more rapid implantation.

Another aim is to provide a more compact osteosynthesis device.

Another aim is to provide an osteosynthesis device comprising a reduced number of separate parts during implantation.

Another aim is to provide an osteosynthesis device wherein the clamping or fastening shows improved reliability.

BRIEF DESCRIPTION OF THE DRAWINGS

The invention, with its characteristics and advantages, will be seen more clearly upon reading the description with reference to the appended figures wherein.

DETAILED DESCRIPTION OF THE DRAWINGS

The osteosynthesis device according to the invention uses the principles of the prior art in terms of the possible application. It can be adapted to screw or hook implants and will be represented here in the case of screw, or pedicular screw, implants. Such a device type may also comprise other components, such as transversal connection bars, not described here but which may be included in the device according to the invention. Due to its advantages in terms of size and easy implantation in reduced spaces, such a device is particularly suitable for entirely internal fitting, i.e. with no part protruding outside the epidermis after the operation. This most frequently consists of a permanent device or one to be kept for a long time.

Figure 1:
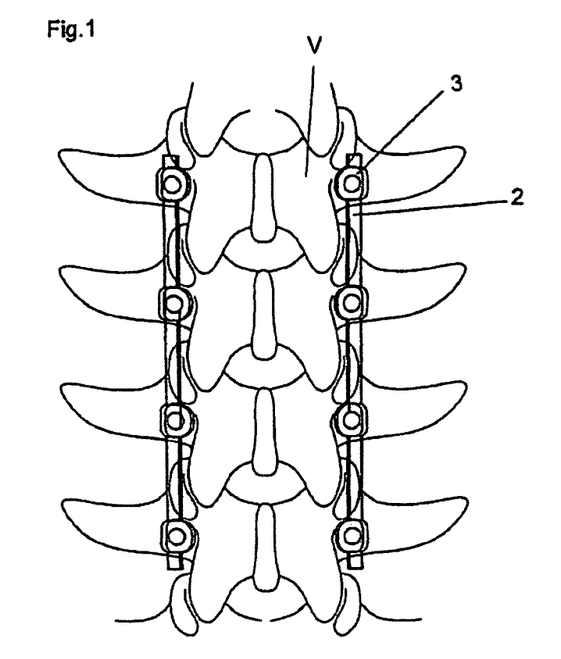
FIG. 1 is a rear view on the spine of an osteosynthesis device according to the invention, in the case of pedicular screw implants.
Figure 2:
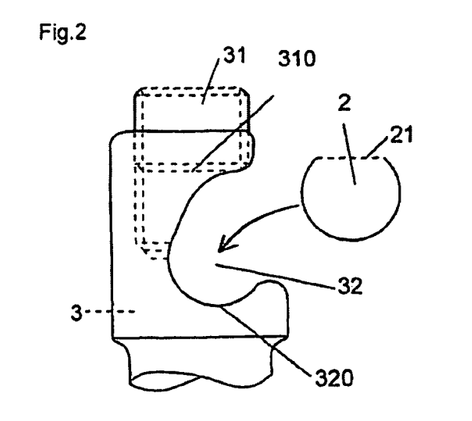
FIG. 2 is a partial side view of the region comprising the fixation of a bar to an implant, at the stage where the bar is presented at the entry of the opening of the implant and where the clamping screw is pre-fitted in the implant.
Figure 3A:
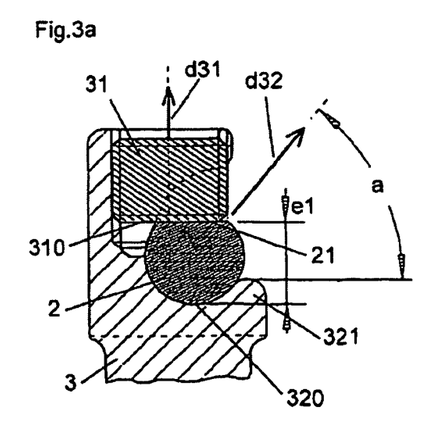
FIGS. 3a and 5 are section side views of a device according to the invention, at the axis of an implant, in an embodiment using a bar comprising a single flat part and for two different bar thicknesses.
Figure 5:
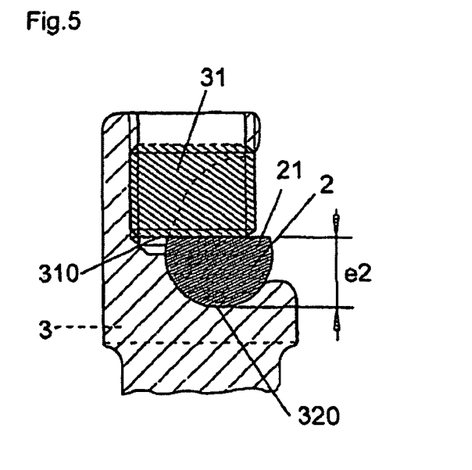

In an embodiment represented in FIGS. 2, 3a and 5, the bar 2 has a rounded cross-section comprising a flat part 21. Said flat part forms a transversal bearing surface, i.e. enabling clamping by supporting the clamping means on said surface, in a direction approximately perpendicular to the longitudinal axis of the bar 2. In its part comprising the fixation means to the bar 2, the implant 3 comprises an opening in the form of a channel 32 passing through the implant along the axis of the bar. Said channel is open on one side of the implant and comprises in one of its edges clamping means moving along an axis perpendicular to the axis of the channel and the bar 2.

Once inserted into the channel 32 of the implant 3, the bar is held by clamping against an internal wall 320 of the channel using clamping means, said means possibly being a clamping screw 31 co-operating with a threaded hole. In the embodiments illustrated in FIGS. 1 to 6, the clamping screw 31 comprises a plane part 310 at its end pressing on the flat part 31 of the bar. As a general rule, said clamping screw may advantageously be of a set screw type so as to minimize its size while retaining the possibility of a long movement along its axis. Said screw comprises gripping means, such as an upper face comprising a recess 312, FIGS. 7 and 8, capable of co-operating with a maneuvering or clamping tool, for example a hexagon socket recess.

In the embodiments described here, the body of the implant is attached to the bone anchorage means, whether they consist of a threaded part (FIG. 6) or one or more hooks (not shown). In this case, the body of the implant itself comprises the clamping means and receives the support bar(s) 2, by direct contact or via intermediate support parts such as rings or distance sleeves.

In the embodiment described here, the clamping screw 31 is screwed into a threaded hole passing through the top edge of the channel 32 and does not overlap onto the opening of said channel and therefore does not obstruct the insertion of the bar 2. Therefore, the clamping screw 31 can be pre-fitted in the implant, thus decreasing the operations during the intervention, the operating time and the risk of the part being lost in the operative field.

Due to the plane contact between the clamping screw 31 and the bar 2, it is possible to use several types of bars, of different thicknesses $e_1$, FIG. 3; $e_2$, FIG. 5, in the same implant model, provided that the cross-section of the bar 2 is of a shape capable of co-operating with the lower wall 320 of the implant channel. Indeed, due to the plane nature of the contact surface 21 of the bar, the clamping screw 31 will clamp the bar 2 in the same way, irrespective of its thickness, provided that its travel is sufficient to come into contact with the flat part 21. Therefore, it is possible to have different bar thicknesses, and therefore different rigidities, for the same implant model, which reduces the stock and type of productions required to cover all requirements. It is also possible to modify rigidity by changing the bar during the operation or during a subsequent operation according to the performances obtained, without having to change the implants, which could represent an injury or additional damage to the vertebrae.

Figure 4A:
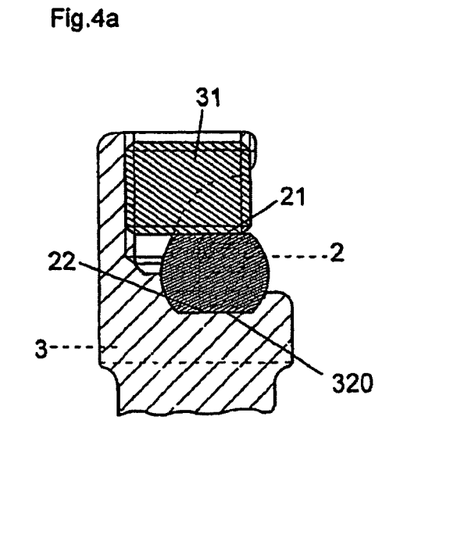
FIG. 4a is a side view of a device according to the invention, at the axis of an implant, in an embodiment using a bar comprising two flat parts.

In another embodiment represented in FIG. 4a, the bar 2 comprises a second flat part 22 opposite the first flat part 21 and approximately parallel to said part, said second flat part 22 forming a bearing surface on the bottom face 320 of the channel 32 of the implant 3. In this arrangement, by means of its co-operation with the wall 320 of the channel, the second flat part 22 of the bar helps ensure the stability and centering of said bar in the channel 32 of the implant during clamping to ensure that the clamping screw 31 is indeed resting perpendicularly on the flat part 21 and therefore provides the best clamping possible. Through this increased stability, this arrangement also ensures improved subsequent reliability of the clamping, by preventing the bar 2 from pivoting around its axis under the effect of forces or vibrations, which would be liable to cause the loosening of the assembly.

In one embodiment, the channel 32 receiving the bar 2 in the implant 3 is of a shape enabling the extension of the bar along an outward direction d32 forming a non-null angle a with a plane perpendicular to the axis of the clamping means 31. To prevent any untimely escape of the bar from the implant, said angle a is oriented in the direction where the outward direction d32 of the bar forms an acute angle with the loosening direction d31 of the clamping means. This means that the clamping means 31 must move in the loosening direction d31 for the bar to be able to move d32 to the channel outlet.

Figure 3B:
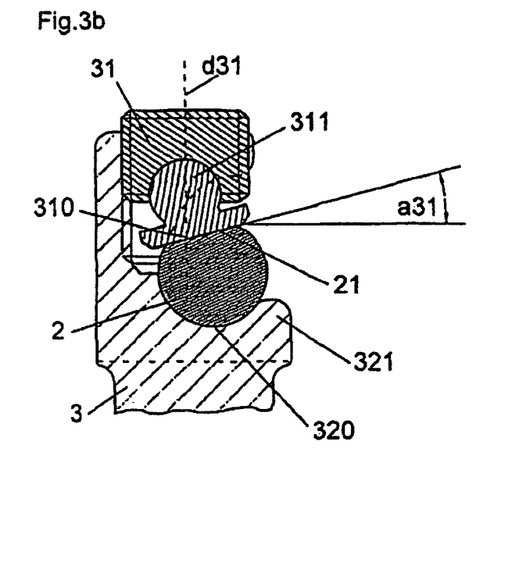
FIG. 3b is a sectional side view of a device according to the invention, at the axis of an implant, in an embodiment comprising a polyaxial clamping screw.

In one embodiment represented in FIG. 3b, the clamping screw 31 comprises a plane bearing surface 310 mounted on a ball joint 311, enabling perfectly flat support on the bar, even if the flat part is not exactly perpendicular to the axis of said clamping screw, in particular when the axes of the different implants are not perfectly parallel. The permissible angle a31 of inclination may for example be of the order of 20 degrees.

The clamping means may be immobilized by any known means, such as glue, the plastic deformation at one or more points of the surfaces co-operating for their movement, or the presence of elastically deformable substances in the threading such as a "Nyl'stop" type locking ring. The only micro-movements remaining possible for the bar are then, at the most, limited to the plane perpendicular to the axis d31 of the clamping means. The movements in this plane, particularly when moving from the base of the channel, are themselves restricted by a part of the bottom edge of the channel, forming an upward nose 321 opposing these movements.

Figure 4B:
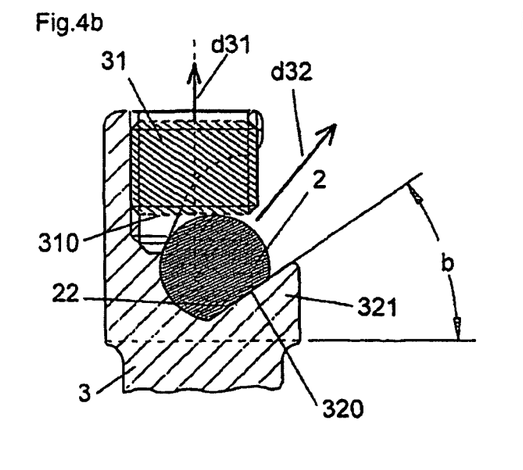
FIG. 4b is a side view of a device according to the invention, at the axis of an implant, in an embodiment using a bar comprising one flat part and an implant comprising an inclined plane surface.

In one embodiment represented in FIG. 4b, the bar 2 comprises a flat part 22 which co-operates with the inner wall 320 of the channel 32 of the implant forming a plane surface, thus ensuring the stability and centering of said bar in the channel 32 of the implant during the clamping of the clamping screw 31. Said plane surface 320 of the implant forms a non-null angle b with a plane perpendicular to the axis d31 of the clamping means. So as to prevent any untimely escape of the bar from the implant, said angle b is oriented in the direction where the outward direction d32 of the bar forms an acute angle with the loosening direction d31 of the clamping means. This means that the clamping means 31 must move in the loosening direction d31 for the bar to be able to move d32 to the channel outlet.

Figure 6:
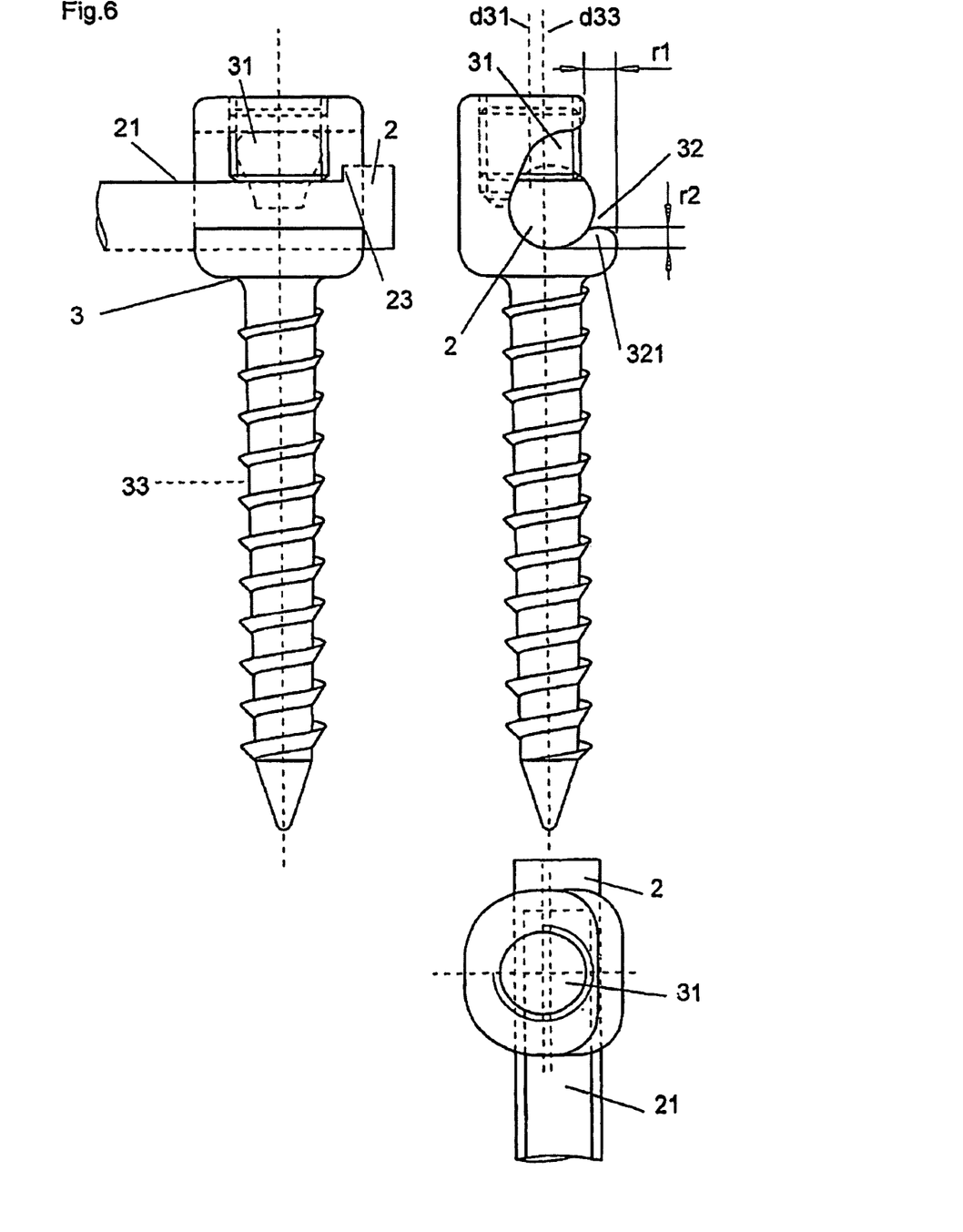
FIG. 6 is a side and top view of an implant according to the invention, in an embodiment using a bar comprising an end with no flat part, in the case of a screw implant.

In one embodiment illustrated in FIG. 6, the support bar 2 comprises one end, or two, comprising no flat part 21. The end of the flat part in this case forms a shoulder 23 which ensures that the bar 2 does not escape from the implant in a direction longitudinal to said bar. Due to this safety device, it is possible only to allow a very short length of bar 2 to protrude from the implant, which reduces the size of the overall device and improves its implantation possibilities at points where anatomical conditions allow little space.

In one embodiment represented in FIG. 6, the implant 3 comprises bone anchorage means composed of one part 33 tapered and threaded in a known way, the bar fixation means and clamping means 31 are in this case located in the end opposite the bone anchorage means. In this embodiment, the axis d31 of the clamping means is parallel to the axis d33 of the bone anchorage means, the clamping being carried out by moving closer to the threaded part, referred to here as the lower part of the implant 3. So as to limit the size of the implant, the axis of the clamping means may be offset by moving away from the inlet of the channel 32 to insert the bar 2 in the implant. In the same way, the top edge of the channel comprises a recess r1 in relation to the bottom edge in its projection along the axis d33 of the implant. Said recess r1 could typically be of the order of 2 mm. So as to provide sufficient clamping, the nose 321 formed by the bottom end of the channel 32 protrudes upwards by a determined height r2 in relation to the plane perpendicular to the axis d31 of the clamping means and via the bottom part of the wall 320 which supports the bar 2 during clamping. Said height r2 could typically be of the order of 2 mm.

For the implantation of an osteosynthesis device according to the method according to the invention, several types of implants, for example screwed or comprising a hook, may be used.

In the case (represented in FIG. 1) of screwed implants, this implantation may be carried out in the part of the vertebra referred to as the pedicle. This type of surgical intervention comprises in this case a step consisting of fixing by screwing the part of the implant 3 provided with a screw pitch 33 on the vertebrae V, for example two implants on each of five vertebrae, by aligning the directions of their respective channels upwards.

During a surgical intervention, if an osteosynthesis device is implanted using the method according to the invention, the use of bars 2 comprising one or more flat parts 21, 22 enables said bars to offer a determined flexibility along a direction perpendicular to said plane faces. Said flexibility is important when bending the bars, necessary to adapt the entire device to the patient's conformation and the modifications that need to be made. The presence of said plane faces also enables the bars to comprise a plane surface on part of their length to comprise accurate implant dimensional references or positioning references.

Due to the fact that implants of the same model can accept several bar thicknesses e1, e2, it will be possible to modify the choice of bar rigidity after fixing the implants, without needing to extract said implants from the vertebrae to insert others, therefore also without damaging the vertebrae further in the case of screwed implants.

In a following step of a method according to the invention (represented in FIG. 2), the arrangement of the opening of the channel 32 of the implant 3 makes it possible to insert the bar 2 in a simple lateral movement, without requiring a longitudinal movement along the axis of the bar as in the case of a clamp.

Since the clamping screw 31 is already in place in the implant 3, the clamping can be carried out without assembling additional parts. Since said clamping screw is supported by a plane part 310 on a plane surface 21 of the bar, the contact surface enabling the clamping will be larger than on a round cross-section bar, directly ensuring high reliability of the connection. Once the clamping screw is in place, the raising of the bottom edge of the channel 32 in the form of a nose 321 prevents any lateral movement of the bar outside the channel.

The clamping may be carried out in several stages, a first progression of the clamping screw making it possible to hold the bar in the implant while allowing freedom of longitudinal movements to adjust the position of the implants on the bar, as required. These adjustments may be composed of a positioning of the implants at different distances from the end of the bar, to adjust the position of the spine in a sagittal plane, i.e. in different positions varying in terms of arching (lordosis) or curvature (cyphosis). Said adjustment may also comprise differences in positioning between the implants of each of two bars arranged at either side of the spine, to adjust the position of the spine in a lateral plane, i.e. in different curvatures inclined to varying degrees on one side of the body or in relation to the pelvis.

Once the desired relative positions of the different components of the devices and the spine have been obtained, the bar will be clamped completely in the implant in another step, as required and according to the progress of the surgical intervention, by completely clamping the clamping screw on the flat part 21 of the bar.

The method according to the invention, by reducing the complexity of the assembly, makes it possible in this way to reduce implantation difficulties, rendering the intervention shorter, less tiring for the operative personnel and less traumatizing for the patient. By reducing the size of the device without affecting the reliability of the assembly, it is also possible to obtain better results and use this technique in a larger number of cases. The possibility to change the bars without removing the implants also makes it possible to envisage a modification of the device more easily in order to adjust the performance according to requirements and the results observed.

In other embodiments, the device according to the invention can use one or more bars 2 comprising in part or all of their length a non-plane transversal bearing surface 21. Said bearing surface is produced by a region where part of the circumference of the bar comprises a convexity lower than the convexity of the rest of the circumference of the bar. A lower convexity in this case refers to a convexity comprising a greater radius of curvature. The contact with a plane surface of the clamping screw 31 or clamping means will then be greater than on a circular circumference and more reliable.

Figure 7:
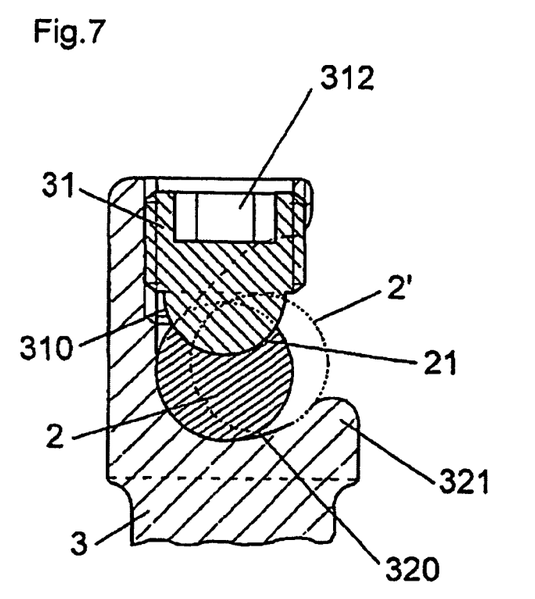
FIG. 7 is a sectional side view of a device according to the invention, at the axis of an implant, in an embodiment using a spherical head clamping screw clamping a bar comprising a recess or a circular cross-section groove complementary to the clamping face.
Figure 8:
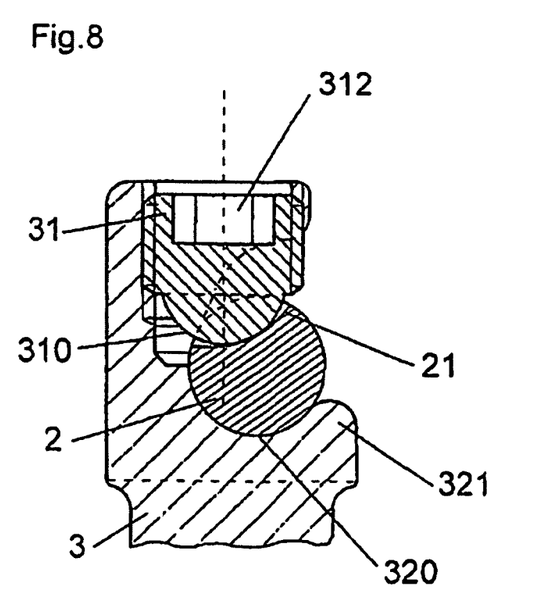
FIG. 8 is a sectional side view of a device according to the invention, at the axis of an implant, in an embodiment using a spherical head clamping screw clamping a bar comprising a recess or a circular cross-section groove of a radius greater than that of the clamping face.

In one embodiment represented in FIGS. 7 and 8, the device according to the invention uses one or more bars 2 comprising a transversal bearing surface 21 showing a face of opposed convexity to the rest of the circumference, i.e. concave. In this embodiment, the clamping means, for example the clamping screw 31, comprise a clamping face 310 showing a convexity in the same direction as the bearing surface 21 of the bar 2. Said clamping surface 310 may in particular show a form of revolution around its screwing axis d31, so that said screwing can be carried out with a progressive approach and a continuous contact on the bar 2.

Depending on the applications, the bar 2 may comprise one or more regions comprising such a transversal bearing surface 21.

Said bearing surfaces may be produced in several regions, contiguous or not, distributed along the bar or on only part of this length. Such a bar may in this way comprise one or more spherical recesses, or oblong recesses with a circular cross-section and spherical ends, or in the form of grooves of circular cross-section transversal to the bar.

Said bearing surfaces may also be produced in several parts of the same section of the bar, i.e. distributed in several different angular positions around the same point located on the axis of the bar. Such a bar may in this way comprise several grooves along its length in different angular positions.

Such position variations thus make it possible to produce a small number of different bar models for numerous anatomical or pathological configurations, by clamping on the most suitable bearing surface. These different clamping point possibilities may also enable easier adjustment of the longitudinal position of the implants in relation to the bar. Indeed, it is possible to insert the bar into the channel of the implant and hold it there by screwing the clamping screw sufficiently, without locking it. The presence of a tapered recess or a plane, convex or concave groove makes it possible to move the implant on the bar before locking.

In the embodiment illustrated in FIG. 7, the clamping surface 310 and the bearing surface 21 comprise approximately complementary cross-sections, transversal to the bar 2. Therefore, clamping is carried out on large contact surface and ensures a good reliability in itself. In this embodiment, the clamping surface 310 may show for example a spherical portion shape. The channel 32 receiving the bar 2 in the body of the implant 3 may then comprise an arc-shaped internal wall 320 wherein the centre coincides with the centre of the clamping 310 and bearing surfaces 21. In this way, it is possible to modify, around said centre, the angular position of the bar in the channel, for example in a slightly offset position 2', to carry out a rotation or de-rotation to adjust the relative angular position of several implants fixed onto the same bar. Due to the arc shape of the internal wall 320 of the base of the channel 32, said adjustment may be carried out without modifying the distance of the bar to the clamping screw and therefore there is no risk of untimely locking or unlocking.

In the embodiment illustrated in FIG. 8, the clamping surface 310 of the clamping screw 31 shows a lower convexity than that of the transversal bearing surface 21 of the bar 2. In this embodiment, the clamping surface 310 may for example show a spherical portion shape. The bearing surface 21 of the bar will show in this case an arc-shaped cross-section, transversal to the bar, of a radius greater than that of the clamping surface 310.

While obtaining a large contact surface between the clamping screw and the bearing surface, such a configuration makes it possible carry out a rotation or de-rotation of the bar to adjust the relative angular position of several implants fixed onto the same bar. It is possible in this case to use a channel 32 wherein the internal wall 320 is complementary to the bar, the angular adjustment of the bar then being possible around the axis of the channel or bar.

In this way, the invention relates to an osteosynthesis device, particularly for the spine by means of internal implantation, comprising firstly one or more bars 2 used to support or move the spine, and secondly at least one implant 3 connecting the bars and the vertebrae V, said implant comprising firstly bone anchorage means attached to the body of said implant and secondly fixation means for said bars, said fixation being carried out by clamping means 31 clamping said bar against the internal walls 320 of a channel 32 formed in said body of the implant 3, characterized in that said bars comprise a transversal bearing surface 21 on at least part of their length, said transversal bearing surface being produced by a section of said bars comprising at least one flat part or part of lower or opposed convexity in relation to the rest of said section.

According to one embodiment, the transversal bearing surface 21 of the bar is composed of at least one concave shaped face, showing the shape of a concave recess or a groove.

According to one embodiment, the clamping means comprise a convex surface which is supported on the recess or groove of the bar 2, thus ensuring good clamping reliability.

According to one embodiment, the transversal bearing surface of the bar is composed of at least one face in the form of a flat part 21.

According to one embodiment, the clamping means comprise a plane surface 310 which is supported on the flat part 21 of the bar 2, thus ensuring good clamping reliability.

According to one embodiment, the clamping means 31 comprise a joint 311, for example a ball joint, between their main body and the plane surface 310 supported on the flat surface 21 of the bar 2, enabling a plane support even if the flat part of the bar forms a non-null angle a31 with a plane perpendicular to the axis d31 of the clamping means.

According to one embodiment, the bars 2 comprise at least one of their ends a part with no flat part or transversal bearing surface over a determined length, said part with no flat part forming a shoulder 23 capable of co-operating with the shape of the implant or clamping means to act as a longitudinal stop on the bars, thus making it possible to reduce the length protruding from the implants 3 located at their ends and therefore to reduce the size of the device.

According to one embodiment, the support bars 2 comprise on a part of their length a plane face 22 co-operating with an internal wall 320 of the channel of the implant forming a plane surface to carry out positioning and stable centering of the bar in said opening.

According to one embodiment, the plane surface 320 of the channel 32 of the implant can form a non-null angle b with a plane perpendicular to 30 the axis d31 of the clamping means, said angle b being oriented in the direction where the clamping means are to be loosened d31 to enable the bar to come out d32 of the base of the channel.

According to one embodiment, the approach distance of the clamping means 31 and the dimensions of the channel 32 of the implant are sufficiently large to receive bars of different thicknesses e1, e2 with the same implant model 3, it being possible to compensate for said differences in thickness with a variation in the position of the clamping means in relation to the opposite wall 320 of the channel.

According to one embodiment, the clamping means 31 are located on only one of the two edges of the channel 32 of the implant 3 and can thus be pre-fitted in the implant without obstructing the insertion of the bar 2 during the surgical intervention.

According to one embodiment, the implant 3 receives the bar 2 in a channel 32 wherein the opening comprises an extension direction d32 forming a non-null angle a with a plane perpendicular to the axis d31 of the clamping means, said angle a being oriented in the direction where the clamping means are to be loosened d31 to enable the bar to come out d32 of the base of the channel.

According to one embodiment, the edge of the channel opposite the clamping means forms a nose 321 which prevents the bar 2 from coming out of the channel 32 perpendicular to the axis of the clamping means 31, for example under the effect of vibrations, wear or crushing of the different surfaces in contact.

According to one embodiment, the clamping means 31 are composed of a clamping screw mounted into a threaded hole passing through one of the edges of the channel 32 receiving the bar 2 in the implant 3.

According to one embodiment, the bone anchorage means of the implant are composed of a tapered and threaded part 33 that can be screwed into a vertebra V, for example into a pedicle.

According to one embodiment, the axis d31 of the clamping screw is approximately parallel to the symmetrical axis d33 of the bone anchorage means of the implant.

According to one embodiment, the top edge of the channel 32 comprising the clamping screw 31 is retracted at the symmetrical axis d33 of the implant in relation to the bottom edge of the channel, limiting the size of the implant in the part-opposite the bone anchorage means.

According to one embodiment, the nose 321 formed by the bottom edge of the channel 32 protrudes by a determined distance r1 in relation to the top edge moving from the axis d33 of the implant and protrudes by a determined distance r2 in relation to the base 320 of the channel, along the axis of the clamping screw and in the loosening direction d31.

According to one embodiment, the bone anchorage means of the implant are composed of a curved part that can be attached to a shape disorder present on a spinal component.

According to one embodiment, the device can be used to perform spinal osteosynthesis in exclusively internal implantation.

The invention also relates to a method to prepare such an osteosynthesis device, characterized in that it comprises a step consisting of inserting the clamping means 31 into the implants 3, said step being carried out prior to the surgical intervention.

It should be clear to those skilled in the art that the present invention allows embodiments in numerous other specific forms without leaving the scope of the invention as claimed. As a result, the present embodiments must be considered as illustrations, but may be modified in the field defined by the scope of the claims attached and the invention must not be limited to the details given above.

The invention claimed is:

1. An osteosynthesis device comprising:
   a bar comprising a generally rounded portion having a substantially flat longitudinal bearing surface extending substantially parallel to a longitudinal axis of the bar along at least a portion of a length of the bar; and
   an implant having a longitudinal axis and comprising
      a channel having an opening along a side of the implant configured to admit the bar into the channel in a direction transverse to the longitudinal axis of the bar and a clamping wall having a clamping surface complementary to the substantially flat longitudinal bearing surface of the bar, the clamping surface forming a non-zero angle with the longitudinal axis of the implant, and
      a clamp having a fully open position providing sufficient clearance in the opening of the channel to admit the bar in the channel, a partially open position configured to loosely retain the bar in the channel, and a clamping position configured to completely clamp the bar to the clamping wall of the channel.

2. An osteosynthesis device comprising:
   a bar comprising a rounded surface and a transversal bearing surface, the rounded surface and the transversal bearing surface extending a first length longitudinally along a first portion of the bar, the bar having a first cross-sectional circumference along the first portion of the bar, the first cross-sectional circumference of the bar having a convexity along the rounded surface of the bar, and the transversal bearing surface being selected from the group consisting of surfaces that are generally flat in the cross-sectional circumference, surfaces that have a convexity less than the convexity along the rounded surface of the bar, and surfaces that are concave in the cross-sectional circumference; and
   an implant comprising
      a body,
      a bone anchor,
      a clamp movably engageable with the body of the implant, the clamp comprising a bearing surface configured substantially complementary to the transversal bearing surface, and
      a channel having an opening along a side of the implant configured to receive the first portion of the bar into the channel in a direction transverse to a longitudinal axis of the bar with the clamp at least partially engaged with the body of the implant.

3. Device according to claim 2 wherein the transversal bearing surface of the bar is concave in the cross-sectional circumference and the bearing surface of the clamp is convex.

4. Device according to claim 3 wherein the transversal bearing surface of the bar has a first radius of curvature, the bearing surface of the clamp has a second radius of curvature, and the first radius of curvature is greater than the second radius of curvature.

5. Device according to claim 2, wherein the transversal bearing surface of the bar is flat in the cross-sectional circumference and the bearing surface of the clamp is flat.

6. Device according to claim 2 wherein the bearing surface of the clamp is articularly disposed by a joint.

7. Device according to claim 2 wherein the bar has at least one end portion comprising a longitudinal stop.

8. Device according to claim 7 wherein the at least one end portion does not have a transversal bearing surface, and the longitudinal stop comprises a shoulder formed at a junction of said end portion with the first portion of the bar having a transversal bearing surface.

9. Device according to claim 2 wherein at an internal wall of the channel of the implant comprises a planar surface configured complementary to a planar face disposed on the bar.

10. Device according to claim 9 wherein the clamp has an axis and the planar surface of the implant forms a non-null acute angle with a plane perpendicular to the axis of the clamp, said angle being oriented toward the opening of the channel.

11. Device according to claim 2 wherein the clamp has an approach distance, and the approach distance of the clamp and the dimensions of the channel of the implant are sufficiently large to receive bars of different thicknesses.

12. Device according to claim 2 wherein the channel has two edges, and the clamp is located along only one of the two edges of the channel.

13. Device according to claim 2 wherein the clamp has an axis and a loosening direction, and the opening of the channel defines an extension direction that forms a non-null angle with a plane perpendicular to the axis of the clamp, said angle being oriented in the loosening direction of the clamp.

14. Device according to claim 2 wherein the clamp has an axis, the channel has an edge opposite the clamp, and the edge of the channel opposite the clamp forms a nose configured to retain the bar in the channel along a direction perpendicular to the axis of the clamp.

15. Device according to claim 2 wherein the channel has at least two edges, and the clamp comprises a clamping screw mountable in a threaded hole passing through one of the edges of the channel.

16. Device according to claim 2 wherein the bone anchor of the implant includes a tapered and threaded part configured to be screwed into a vertebra.

17. Device according to claim 16 wherein the clamp includes a clamping screw having an axis, the bone anchor has a symmetrical axis, and the axis of the clamping screw is approximately parallel to the symmetrical axis of the bone anchor.

18. Device according to claim 17 wherein the channel has a top edge along which the clamping screw is disposed and a bottom edge disposed proximal to the bone anchor, and the top edge of the channel is retracted toward the symmetrical axis of the bone anchor in relation to the bottom edge of the channel.

19. Device according to claim 18 wherein the top edge of the channel extends a first distance from the symmetrical axis of the bone anchor, the bottom edge of the channel forms a nose that protrudes by a second distance from the symmetrical axis of the bone anchor, and the second distance is greater the first distance.

20. Device according to claim 2 wherein an edge of the channel and the bearing surface of the clamp define more than one clamping position for the bar, each clamping position having an angular orientation, with the angular orientation of the bar being distinct in each clamping position.

21. Device according to claim 2 wherein the bone anchor of the implant comprises a curved part configured for attachment to a shape disorder present on a spinal component.

22. Device according to claim 2 wherein the bar and the implant are configured for exclusively internal implantation in spinal osteosynthesis.

23. Device according to claim 2 wherein the bar has a cross-sectional circumference along at least a second portion of the bar, the bar along the second portion comprising a transversal bearing surface selected from the group consisting of surfaces that are flat in the cross-sectional circumference, surfaces that have a convexity less than the convexity of the rest of the cross-sectional circumference, and surfaces that are concave in the cross-sectional circumference, and the transversal bearing surface of the first portion of the bar is not contiguous with the transversal bearing surface of the second portion of the bar.

24. Device according to claim 2 in which the first length is equal to the length of the rod.

25. Device according to claim 2 in which the first length is less than the length of the rod.

26. Device according to claim 2 having plural transverse bearing surfaces.

27. An osteosynthesis device comprising:
a bar comprising a generally rounded portion having a substantially flat longitudinal bearing surface extending substantially parallel to a longitudinal axis of the bar along at least a portion of a length of the bar; and
an implant comprising
a channel having a clamping wall and an opening along a side of the implant configured to admit the bar into the channel in a direction transverse to the longitudinal axis of the bar, and
a clamp having a substantially flat clamping surface complementary to the substantially flat longitudinal bearing surface of the bar, the clamp having a fully open position providing sufficient clearance in the opening of the channel to admit the bar in the channel, a partially open position configured to loosely retain the bar in the channel, and a clamping position configured to completely clamp the bar to the clamping wall of the channel.

28. The osteosynthesis device of claim 27 in which the bar comprises plural substantially flat longitudinal bearing surfaces extending substantially parallel to the longitudinal axis of the bar along at least a portion of the length of the bar.

29. The osteosynthesis device of claim 28 in which the clamping wall of the channel is complementary to one of the flat longitudinal bearing surfaces of the bar.

30. The osteosynthesis device of claim 27 in which the clamp comprises a clamping screw disposed in a threaded hole of the implant.

31. The osteosynthesis device of claim 27 in which the implant comprises a nose adjacent to the opening of the channel.

32. The osteosynthesis device of claim 27 in which the clamp comprises a body and a joint connecting the clamping surface to the body.

33. The osteosynthesis device of claim 27 in which the bar comprises a longitudinal stop.

34. The osteosynthesis device of claim 33 in which the longitudinal stop is a shoulder.

35. An osteosynthesis device comprising:
a bar comprising a generally convex rounded portion having a substantially arcuate longitudinal bearing surface extending substantially parallel to a longitudinal axis of the bar along at least a portion of a length of the bar; and
an implant comprising
a channel having a clamping wall and an opening along a side of the implant configured to admit the bar into the channel in a direction transverse to the longitudinal axis of the bar, and
a clamp having a substantially arcuate clamping surface complementary to the substantially arcuate longitudinal bearing surface of the bar, the clamp having a fully open position providing sufficient clearance in the opening of the channel to admit the bar in the channel, a partially open position configured to loosely retain the bar in the channel, and a clamping position configured to completely clamp the bar to the clamping wall of the channel.

36. The osteosynthesis device of claim 35 in which the clamp comprises a clamping screw disposed in a threaded hole of the implant.

37. The osteosynthesis device of claim 35 in which the implant comprises a nose adjacent to the opening of the channel.

38. The osteosynthesis device of claim 35 in which the arcuate longitudinal bearing surface has a general convexity less than a general convexity of the rounded portion of the bar.

39. The osteosynthesis device of claim 35 in which the arcuate longitudinal bearing surface is concave.

40. The osteosynthesis device of claim 35 in which the bearing surface comprises an oblong recess along the bar.

41. The osteosynthesis device of claim 35 in which the bearing surface comprises a groove along the bar.

42. The osteosynthesis device of claim 35 in which the clamp comprises a body and a joint connecting the clamping surface to the body.

43. The osteosynthesis device of claim 42 in which the joint is a ball joint.

44. The osteosynthesis device of claim 35 in which the bar comprises a longitudinal stop.

45. The osteosynthesis device of claim 44 in which the longitudinal stop is a shoulder.

* * * * *